United States Patent [19]

Jankewitz

[11] Patent Number: 4,666,709

[45] Date of Patent: May 19, 1987

[54] NAIL COATING MATERIAL AND DEVICE FOR APPLYING THE SAME

[75] Inventor: Axel Jankewitz, Fürth, Fed. Rep. of Germany

[73] Assignee: A.W.Faber-Castell GmbH & Co., Stein, Fed. Rep. of Germany

[21] Appl. No.: 820,444

[22] Filed: Jan. 17, 1986

Related U.S. Application Data

[63] Continuation of Ser. No. 558,855, Dec. 7, 1983.

[30] Foreign Application Priority Data

Dec. 21, 1982 [DE] Fed. Rep. of Germany ....... 3247172

[51] Int. Cl.⁴ ................................................ A61K 7/04
[52] U.S. Cl. ......................................... 424/61; 424/78
[58] Field of Search ....................... 401/196, 198, 199; 424/61, 78

[56] References Cited

U.S. PATENT DOCUMENTS

| | | | |
|---|---|---|---|
| 3,089,182 | 5/1963 | Lofgren | 401/199 |
| 3,216,983 | 11/1965 | Shelanski et al. | 424/61 |
| 3,231,924 | 2/1966 | Lofgren | 401/198 |
| 3,849,547 | 11/1974 | Kalopissis | 424/61 |
| 3,993,409 | 11/1976 | Hart | 401/199 |
| 4,082,467 | 4/1978 | Kaplan | 401/199 |
| 4,126,675 | 11/1978 | Boulogne et al. | 424/61 |
| 4,158,053 | 6/1979 | Greene et al. | 424/61 |
| 4,301,046 | 11/1981 | Schlossman | 424/61 |
| 4,302,442 | 11/1981 | Socci et al. | 424/61 |
| 4,309,522 | 6/1983 | Jacquet et al. | 424/61 |

FOREIGN PATENT DOCUMENTS

| | | | |
|---|---|---|---|
| 57-0050980 | 3/1982 | Japan | 424/61 |
| 1029339 | 11/1966 | United Kingdom | 401/198 |

Primary Examiner—William R. Dixon, Jr.
Assistant Examiner—Margaret B. Medley
Attorney, Agent, or Firm—Michael J. Striker

[57] ABSTRACT

A highly fluid ink-like nail coating material has the following composition: 10-50 weight-% of an alkali-soluble polyester resin with an acid number of at least 60, 0.7-15.0 weight-% of 25% $NH_3$ solution or the equivalent quantity of highly volatile, low-molecular aliphatic amine, 0-15 weight-% of at least one cosmetically approved acid organic coloring substance, 0-50% additive, and water in a quantity to complete the components to 100 weight-%. It can be applied onto fingernails and toenails, because of its low viscosity, by an application device having a supply container filled with this nail coating material and a wick extending from the interior of the supply container outwardly.

11 Claims, 1 Drawing Figure

U.S. Patent    May 19, 1987    4,666,709
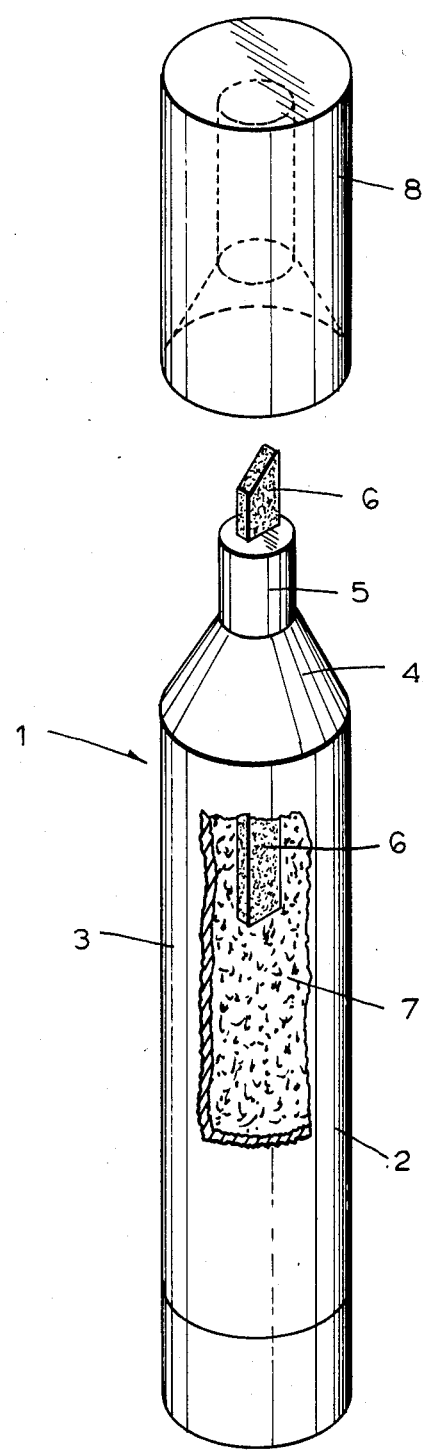

NAIL COATING MATERIAL AND DEVICE FOR APPLYING THE SAME

This is a continuation of application Ser. No. 558,855 filed Dec. 7, 1983.

BACKGROUND OF THE INVENTION

The present invention relates to a nail coating material and a device for applying the same. More particularly, it relates to a resin-containing, pigment-free, and in some cases coloring substance-containing nail coating material with a low viscosity. It also relates to the utilization of such a nail coating material in form of an ink for filling of a capillary application device, for example a wick pencil. The nail coating material, as well as the capillary application device filled therewith, serve for coating of fingernails and toenails.

Nail coating materials are produced as more or less viscous liquids which are applied onto the nails with the aid of a brush. A base of the coating material is in general nitrocellulose, in some cases in mixture with suitable resins, as well as with addition of pigments and/or suitable coloring substances. The above mentioned substances are water-insoluble, and therefore they must be dissolved in organic solving media, such as butylacetate, ethylacetate, in some cases with addition of benzene or toluene. Compositions of such known nail coating materials are disclosed, for example, in "Taschenbuch der Modernen Parfümerie und Kosmetik" by H. Janistyn, 4th Edition, 1974, page 681. The known nail coating materials can be applied, because of their high viscosity and also because their pigment content, exclusively by the brush. The organic substances used as solving media are burnable and have the properties to engage the skin and the nail layer in degreasing manner.

SUMMARY OF THE INVENTION

Accordingly, it is an object of the present invention to provide a low-viscosity nail coating material which can be formed on the basis of water or generally water-alcohol mixtures and because of its completely pigment-free composition (in connection with the above mentioned low viscosity) can be applied with applicators other than brushes.

In keeping with these objects and with others which will become apparent hereinafter, one feature of the present invention resides, briefly stated, in a resin-containing, pigment-free, in some cases coloring-substance-containing nail coating material which includes 10-50 weight-% of alkali-soluble polyester resin with an acid number of at least 60, 0.7-15.0 weight-% of 25% $NH_3$ solution or the equivalent quantity of highly volatile low-molecular aliphatic amine, 0-15 weight-% of at least one cosmetically approved acid, organic coloring substance, 0-50 weight-% of additive, and a water in a quantity which completes the quantities of the components to 100 weight-%.

Another feature of the present invention is the utilization of the above mentioned nail coating material as a nail coating ink for filling of a capillary applicating device, for example a wick pencil.

Still another feature of the present invention is a device for coating of the fingernails and toenails, which includes a supply container containing the above mentioned nail coating material, an applying wick extending from the interior of the supply container outwardly, and a cover arranged to close the container during non-use.

The novel features which are considered characteristic for the present invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The single FIGURE of the drawing is a perspective view showing a device for applying a nail coating material in accordance with the present invention.

DESCRIPTION OF THE PREFERRED EMBODIMENTS

A resin-containing, pigment-free, and in some cases coloring-substance-containing nail coating material includes 10-50 weight-% (preferably 25-35 weight-%) of alkali-soluble polyester resin with an acid number of at least 60 (preferably at least 80), 0.7-15.0 weight-% (preferably 1-10 weight-%) of 25% $NH_3$ solution or the equivalent quantity of highly voltaile, low-molecular aliphatic amine, 0.15 weight-% (advantageously 5-12 weight-%) of at least one cosmetically approved acid organic coloring substance, 0-50 weight-% of additives, and water in a quantity to complete the quantity of the components to 100 weight-%.

The alkali-soluble polyester resin with an acid number of at least 60, better more than 80, is suitable for providing a fast drying and at the same time well film-forming basis for ink-like nail coating material. Water resin solution with 10-50 weight-%, advantageously 25-30 weight-%, of this substance can be brought with relatively small quantities of ammonia solution, for example 0.7-15.0 weight-% (advantageously 1-10 weight-%), of a 25% $NH_3$ solution or with the equivalent quantity of highly volatile, low-molecular, aliphatic amine in solution or at least in stable water dispersion. The solutions react because of their low ammonia- or amine-content slightly alkaline, which places them in a position that acid organic coloring substances which are approved in cosmetics are dissolved with formation of salt. In this manner, a low-viscosity liquid is produced, whose viscosity is a maximum of 200 cp and which can be applied easily with the aid of a tampon, a cotton swab, or a wick pencil, then it dries fast and forms a glossy lacquer coat.

It is advantageous when the coating material is provided with additives in form of 0-50 weight-% which is suitable for film formation and/or increase of the adhesive strength and breakage strength of the produced coating. The types of additives used here will be explained in detail hereinbelow. The above given percentages of components are percentages by weight. The quantities of the components are selected such as to form together 100 weight-%.

As the alkali-soluble polyester resin with an acid number of at least 60, preferably at least 80, especially polyphthalic acid-containing resins are taken into consideration. Both terephthalic acid and orthophthalic acid can be used, which in a known manner are esterified with suitable multivalent alcohols, for example glycols, glycerines, erythrites, pentaerythrites, and the like. The esterification is conducted so that only a sufficient number of free non-esterified carboxyl groups remain which provide the above mentioned acid number.

Instead of the tere- and ortho-phthalic acids, also maleic acids, malonic acids, succinic acids, adipic acids as well as their anhydrides can be used. Resins of this type are generally known. There also are known their alkali solubility as well as their utilization, for example in printing inks industry and lacquers industry.

The free non-esterified carboxyl groups of the above mentioned polymers must be converted to bring about the water solubility into alkali-, ammonia- or amino-salts. It is suitable in many cases to use a 25% aqueous $NH_3$ solution which is added to the aqueous resin suspension in the predetermined quantities. Instead of the $NH_3$ solution, also simple, non-toxic amines can be used, such as dimethylamine, diethylamine, triethylamine, diethanolamine, triethanolamine, or similar compositions. In these compositions ammonia is advantageous, since, in this case a somewhat available excess evaporates in the easiest manner and does not possess any unacceptable odors.

The above mentioned resin solutions must be provided with a coloring substance when the nail coat ink is to have a color. Pigments must be avoided if possible. Instead of pigments, cosmetically acceptable acid organic coloring substances, for example triphenylmethane coloring substances or monoazo coloring substances must be introduced.

For improving the formation of film it is recommended when as additive to the base lacquer 0–20 weight-% (preferably 7–12 weight-%) of vinyl pyrolidone-vinylacetate interpolymer is added. Depending upon the employed resin and coloring substance, without the addition of such an interpolymer it is possible that because of unfavorable surface tension the film applied on the nail can form bubbles during drying. This undesirable phenomenon is prevented by the above mentioned interpolymer additions.

Furthermore, it is advantageous when as additive, additionally 5–30 weight-%, preferably 15–25 weight-%, of at least one alcohol with 2–4 C-atoms is used. For this purpose there can be considered ethyl alcohol, n-propylalcohol, i-propylalcohol, as well as the three butylalcohols, n-butanol, i-butanol and tert-butanol. The addition of these alcohols provides for a further reduction of the surface tension of the resin solution, lowering of the viscosity, and thereby providing improved spreading properties.

Finally, it is advantageous when as additive, additionally 0–15 weight-% (preferably 5–10 weight-%) of shellac is used, in form of the whitest possible remaining shellac. This shellac provides a high hardness of the dried film as well as improved water resistance.

The nail coating material or nail polish-ink is illustrated by several examples presented hereinbelow.

For manufacture of the given compositions, first coloring substance mixtures must be produced.

Coloring Substance Mixture I: neutral-red 27 weight-% eosin-S13 (2,4,5,7-tetrabromofluorescein)
33 weight-% erythrosin I (2,4,6,7-tetraiodofluorescein; 2-Na-salt)
40 weight-% eosin acid (4,5-dibromofluorescein)

Coloring Substance Mixture II: violet

33% Alizarin violet (1,5-bis(o-sulfo-p-tuluyl)anthraquinone; Na-salt)
33.3% eosin-S13 (2,4,5,7-tetrabromofluorescein)
33.3% eosin acid (4,5-dibromofluorescein)

With the utilization of these coloring substance mixtures the following nail polish-inks are prepared:

Mixture 1

25 weight-% saturated terephthalic acid ester resin, acid number 110
17 weight-% vinylpyrrolidone-vinylacetate-interpolymer
17 weight-% isopropylalcohol
8 weight-% ethyl-lactate
7 weight-% 25% $NH_3$-solution
0.2 weight-% preservative (quaternary ammonium compound)
10 weight-% coloring substance mixture I water added to 100 weight-%.

Mixture 2

25 weight-% maleic resin, acid number 200
5 weight-% vinyl pyrrolidone-vinylacetate interpolymer
30 weight-% ethanol
10 weight-% 25% $NH_3$ solution
0.2 weight-% preservative (quaternary ammonium compound)
water added to 100 weight-%

Mixture 3

35 weight-% terephthalic acid polyester resin acid number 200
5 weight-% shellac
25 weight-% n-propanol
8 weight-% 25% aqueous $NH_3$ solution
0.2 weight-% preservative (quaternary ammonium compound)
8 weight-% coloring Substance Mixture II
water added to 100 weight-%

All compositions can be easily spread to form films on fingernails or toenails. They dry in less than 2 mintutes so as to form a glossy and firmly adhering film. The obtained viscosity is:

Mixture 1: 130 cp
Mixture 2: 32 cp
Mixture 3: 65 cp

Since with the above presented compositions there are clear transparent low-viscosity solutions, they can be applied easily with the aid of a capillary application device, for example a wick pencil. The utilization of such pencils is especially practical. With such pencil it is easy to produce a clean color design on fingernails and toenails, when the application must be carried out quickly, or when the user is clumsy as is frequently the case for a righthanded person who must work with his or her left hand.

A capillary application device which can be used in accordance with the present invention is shown in the FIGURE as an example.

An applicator is identified as a whole with reference numeral 1. It has a main part 2 and a cover 8. The main part 2 includes a tubular supply container 3 for the nail polish-ink. The supply container 3 conically decreases in its upper part 4 and merges into a tubular part 5. An application wick 6 is arranged in the tubular part 5. It extends downwardly into the supply container 3.

The inventive nail polish-ink can be directly filled into the supply container 3. However, it is advantageous when a tampon 7 or a porous filler of a fibrous material is accommodated in the interior of the supply container. The tampon or the filler absorbs the nail polish-ink, and during the use transfers the same to the wick 6.

During the periods of non-use of the device, the clogging of the wick must be avoided. This is attained in a known manner by placing the cover 8 onto the main part 2.

It will be understood that each of the elements described above, or two or more together, may also find a useful application in other types of compositions and constructions differing from the types described above.

While the invention has been illustrated and described as embodied in a nail coating material and a device for applying the same, it is not intended to be limited to the details shown, since various modifications and structural and compositional changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims; I claim:

1. A resin-containing, pigment-free nail coating material particularly for applying with capillary devices, comprising:
   10–50 weight-% of an alkali-soluble polyester resin with an acid number of at least 60;
   0.7–15.0 weight-% of 25% $NH_3$ solution or the equivalent quantity of highly volatile, low molecular aliphatic amine;
   0.1–15.0 weight-% of at least one cosmetically approved acid organic coloring substance; 2–20 weight-% additive comprising a film forming polymer or interpolymer soluble in water or $C_2$–$C_4$ alcohols;
   water in a quantity completing the quantity of the components to 100 weight-%.

2. A nail coating material as defined in claim 1, wherein said alkali-soluble polyester resin is used in a quantity of 25–35 weight-%.

3. A nail coating material as defined in claim 1, wherein said alkali-soluble polyester resin has an acid number of at least 80.

4. A nail coating material as defined in claim 1, wherein said 25% $NH_3$ solution is used in a quantity of 1–10 weight-%.

5. A nail coating material as defined in claim 1, wherein said cosmetically approved acid organic coloring substance is used in a quantity of 5–12 weight-%.

6. A nail coating material as defined in claim 1, wherein said additive is vinyl pyrrolidone-vinyl acetate interpolymer used in a quantity of 2–20 weight-%.

7. A nail coating material as defined in claim 6, wherein said vinyl pyrrolidone-vinyl acetate interpolymer is used in a quantity of 7–12 weight-%.

8. A nail coating material as defined in claim 1, and further comprising a further additive including at least one alcohol having 2–4 C-atoms.

9. A nail coating material as defined in claim 8, wherein said further additive is used in a quantity of 15–25 weight-%.

10. A nail coating material as defined in claim 1 and further comprising a further additive including shellac in a quantity of 2–15 weight-%.

11. A resin-containing, pigment-free nail coating material particularly for applying with capillary devices, comprising:
    10–50 weight-% of an alkali-soluble polyester resin with an acid number of at least 60;
    0.7–15.0 weight-% of 25% $NH_3$ solution or the equivalent quantity of high volatile, low molecular aliphatic amine;
    0.1–15. weight-% of at least one cosmetically approved acid organic coloring substance selected from the group consisting of
    coloring substance mixture I: neutral red comprising
    27 weight-% eosin-S13 (2,4,5,7-tetrabromofluorscein)
    33 weight-% erythrosin I (2,4,6,7-tetraiodofluorescein; 2-Na-salt)
    40 weight-% eosin acid (4,5-dibromofluorescein), and
    coloring substance mixture II: violet comprising
    33 weight-% alizarin violet (1,5-bis(o-sulfo-p-tuluyl-)anthraquinone; Na-salt)
    33.3 weight-% eosin-S13 (2,4,5,7-tetrabromofluorescein)
    33.3 weight-% eosin acid (4,5-dibromofluorescein)
    2–20 weight-% additive comprising a film forming polymer of interpolymer soluble in water or $C_2$–$C_4$ alcohols;
    water in a quantity completing the quantity of the components to 100 weight-%.

* * * * *